United States Patent [19]

Lok et al.

[11] Patent Number: 4,490,480

[45] Date of Patent: Dec. 25, 1984

[54] NICKEL CATALYST ON ALUMINA SUPPORT

[75] Inventors: Cornelis M. Lok, Rockanje; Dirk Verzijl, Barendrecht; Jacob van Dijk, Maassluis, all of Netherlands

[73] Assignee: Internationale Octrooi Maatschappij "Octropa"B.V., Rotterdam, Netherlands

[21] Appl. No.: 486,513

[22] Filed: Apr. 19, 1983

[30] Foreign Application Priority Data

Apr. 23, 1982 [NL] Netherlands ............... 8201696

[51] Int. Cl.$^3$ .................. B01J 21/04; B01J 23/74; B01J 23/88
[52] U.S. Cl. ..................... 502/315; 502/335; 518/715
[58] Field of Search .......... 502/315, 335; 518/715

[56] References Cited

U.S. PATENT DOCUMENTS

| | | | |
|---|---|---|---|
| 3,235,515 | 2/1966 | Taylor | 502/337 |
| 3,312,635 | 4/1967 | Liquori | 502/315 |
| 4,191,664 | 3/1980 | McArthur | 502/335 |
| 4,410,637 | 10/1983 | Kortbeek et al. | 518/715 X |

FOREIGN PATENT DOCUMENTS 1070633 12/1959 Netherlands.

*Primary Examiner*—W. J. Shine
*Attorney, Agent, or Firm*—Cushman, Darby & Cushman

[57] ABSTRACT

The invention provides new catalysts, useful for various hydrogenation reactions, which consist of 5 to 40% (w/w) of nickel upon a transition alumina, in particular gamma alumina support. These catalysts have an active nickel surface area of between 80 and 300, preferably 100–250 m$^2$/g of nickel and the nickel crystallites have an average diameter of 1 to 5, preferably 1.5 to 3 nanometers. The nickel crystallites are dispersed for at least 95% in the pores of the alumina.

12 Claims, No Drawings

NICKEL CATALYST ON ALUMINA SUPPORT

The invention relates to nickel upon alumina catalysts, their preparation and their use in various hydrogenation reactions.

Nickel catalysts are almost always fixed on a carrier and in this respect there is a wide choice of materials such as silica, guhr, magnesia, aluminium silicate, alumina etc.

The present invention deals with nickel catalysts upon alumina as a support, more in particular nickel upon a transition alumina.

By a transition alumina is understood here the intermediate forms which are obtained by thermal decomposition of aluminium hydroxide. These transition aluminas contain less than 0.5 mol of water per mole of $Al_2O_3$, depending on the temperature up to which they have been treated. The best known transition aluminas are known under the names of gamma, eta and chi (these are only partly crystallized), as well as kappa, theta and delta, the last three being better crystallized than the first three.

For the present invention it is preferred to use gamma-alumina as carrier. The transition alumina used usually has a surface area of 45 to 350 $m^2/g$, preferably 75 to 250, more preferably 90–115 $m^2/g$, and a pore volume of 0.3 to 0.7 l/kg, the particle size being from $10^{-5} - 10^{-2}$ m.

It is advantageous to use predominantly spherical material for fluidized bed techniques; however, for fixed bed techniques extrudates or pellets are preferred. For slurry hydrogenations powders are preferred.

Nickel upon transition alumina catalysts are known in the prior art, inter alia from U.S. Pat. No. 4,191,664 (McArthur), in which such a catalyst is disclosed, which is said to be suitable for the fluidized bed technique. This catalyst consists of nickel on gamma-alumina and was obtained by the precipitation of nickel hydroxide from an ammoniacal solution in which boehmite particles (an alumina hydrate) had been suspended. At a pH value that was dropping because of boiling (which pH was originally 8.9), a precipitate was formed which, after washing, drying, grinding and calcining, consisted of gamma-alumina, because during the calcining (which takes place at abt. 400° C. (750° F.)), the boehmite is converted into gamma-alumina. This catalyst appeared to have a reasonably good activity for methanation, its wear resistance and service life, especially in a fluidized bed, appeared to be unsatisfactory.

The active nickel surface of the nickel upon alumina catalyst disclosed therein appeared to be in the order of magnitude of 50–55 $m^2/g$ Ni. Therefore, these catalysts are not quite satisfactory for other hydrogenation reactions. Also the size of the nickel oxide crystallites is stated to be on the high side, viz. 5–60 nanometers. Finally it is stated that preformed gamma-alumina is much less reactive with nickel compounds than is alumina hydrogel.

The present invention provides nickel upon alumina catalysts containing 5 to 40% (w/w) of nickel having an active nickel surface between 80 and 300 $m^2/g$ Ni, in which the nickel crystallites have an average diameter of 1 to 5 nanometers. In a preferred embodiment the active nickel surface ranges beween 100 and 250 $m^2/g$ Ni; also the average size of the nickel crystallites may then range between 1.5 and 3 nanometers.

The nickel is dispersed for at least 95% in the pores of the alumina (i.e. on the internal surface) and the degree of reduction of nickel oxide to nickel is normally at least 50% (reduction for 30 minutes at 500° C. with 15 $m^3$ $H_2$ (STP) per kg nickel).

It has now been found that catalysts of this type can be conveniently prepared by heating an aqueous suspension or mixture of a transition alumina in a dissolved nickel amine complex for some time to a temperature of 60°–100° C., preferably 75°–95° C., which causes the precipitation of nickel hydroxide, whereafter the catalyst suspension is separated off and, if desired, washed, thereafter dried and calcined to nickel oxide and, if need be, reduced. Alternatively, alumina pellets or extrudates are impregnated with a concentrated solution of a nickel amine complex; subsequently nickel is precipitated by temperature increase.

The precipitation of the nickel hydroxide on the carrier can occur under various conditions. Thus, the precipitation temperature of the suspension is generally between 60° and 100° C., preferably between 75° and 95° C., depending on the alumina particle size. During the precipitation, the suspension generally has a pH value between 11.5 and 9.5. Besides, the pH value generally drops during the heating and, optionally, stirring, because the nickel ammonium complex slowly decomposes and deposits nickel hydroxide on the internal and external surfaces of the carrier particles. This precipitation by heating generally takes from 15 min. to 24 hours, preferably 1–8 hours.

Further, the precipitation generally takes place in concentrations such that the final precipitate contains nickel in weight percentages between 5 and 40, preferably between 15 and 25. Finally, the amount of alumina is generally about 25–150 g/l.

In order to lower the susceptibility of the nickel catalyst to poisoning, particularly with sulphur and/or carbon, it is often advantageous to incorporate in the catalyst a small amount of another metal compound as promoter. Suitable promoters are particularly the elements molybdenum, lanthanum, barium, calcium, copper, potassium and their compounds, molybdenum being preferred. The promoter can be incorporated in the suspension from which it is later precipitated, but it can also be incorporated in the catalyst by spraying or impregnation, both beforehand and afterwards.

After the precipitation of the catalyst, the green cake is generally separated by filtration, and, at choice, the cake is subsequently washed and dried. Sometimes impregnation with an aqueous solution of a promoter compound was carried out subsequently, and, optionally drying and grinding to powder of the proper size were carried out, followed by, again optionally, calcining at a temperature of 300°–500° C.

It has appeared that the right choice of the starting carrier material is important for good results in specific applications and influence, inter alia, wear resistance, maximum service life, activity and selectivity of the final catalysts.

If boehmite, an alumina hydrate, is used as a carrier according to the prior art cited above, and nickel compounds are precipitated on it and subsequently converted by calcining into nickel oxide on gamma-alumina, the result obtained after reduction, particularly with respect to active nickel surface area, wear resistance and maximum service life, is not good, whereas if a preformed transition aluminium trioxide suitable for that purpose is used, especially a suitable gamma $Al_2O_3$, excellent catalysts with improved properties, such as high active nickel surface area and high wear resistance, are obtainable.

The wear resistance, which is not only important for fluidized bed technique but also for fixed bed technique, is evaluated as follows for a fluidisable catalyst:

Standardized forced wear resistance test: The catalyst (50 g) is fluidized by blowing air (425 l/h) through three holes of 0.35 mm in a round bearing sheave and the fines formed by attrition are discharged and collected. After periods of 30 minutes each, the amount of the fines collected is determined by weighing. The percentage of attrition is determined from the following equation:

$$\% \text{ attrition} = 100 \times \frac{\% \text{ fines (time } t) - \% \text{ fines (initial)}}{100 - \% \text{ fines (initial)}}$$

If this percentage of attrition (A) is plotted against the time (t), a straight line is obtained of which the angle of inclination is a measure of wear resistance. This line can be represented by the equation: $A = m\, t = c$. In the case of the catalyst prepared according to Example 1 of U.S. Pat. No. 4,191,664, m was determined in this way as 7.7.

It has now been found that catalysts with a considerably better active nickel surface area, better wear resistance and longer service life can be prepared by heating an aqueous suspension of a transition alumina in a dissolved nickel amine complex for some time to a temperature of 60°–100° C., preferably 75°–95° C., which causes the precipitation of nickel compounds, whereafter the catalyst suspension is separated off and, if desired, washed, thereafter dried, optionally calcined to nickel oxide and, if need be, reduced. Calcining has to be carried out under mild conditions, so as to retain good properties by preventing sintering of nickel oxide crystallites.

The catalysts according to the present invention contain metallic nickel (after reduction), which has been distributed over the internal and external surfaces of the carrier particles, and optionally an amount of promoter, e.g. molybdenum oxides, in an amount ranging between 0.2 and 14% (based on total catalyst). The amount of nickel in the final catalyst is generally 5–40%. Preferably the catalyst contains 15–25% of nickel. Also the catalyst may contain 4–10% of molybdenum.

The catalysts according to the present invention are very useful for the hydrogenation, particularly of fatty materials, such as fatty acids, their esters, and for methanation.

By methanation is understood the preparation of methane-containing gas mixtures from mixtures which contain especially a carbon oxide (monoxide and/or dioxide) and hydrogen. This reaction is especially important for the preparation of substitute natural gas (SNG) from synthesis gas and similar gas mixtures, including those obtained by gasifying coals together with water and oxygen.

In an embodiment of the invention the methanation reaction is carried out continuously with the catalyst in a fluidized bed, this especially because then a better temperature control is possible. However, working with a fluidized bed makes heavy demands on the wear resistance, and this is one of the factors determining its service life (m values ranging between 1 and 2.5 for the catalysts of the invention).

In another embodiment of the invention the methanation reaction is carried out continuously with a fixed bed catalyst, because at high exit temperatures a good thermal stability of the catalyst is required. The present catalysts have been shown to be stable at temperatures up to 700° C.

In a further embodiment of the invention the catalysts are used in the fixed bed hydrogenation of fatty materials such as acids, nitriles, alcohols and esters, in particular triglycerides. The activity and poison resistance of the novel catalysts are improved as a result of their high active nickel surface area. In the case of fatty acid hydrogenation a dramatic improvement in colour of the fatty acids was noted. Hydrobleaching of fatty materials during which the iodine value almost remains constant is also included.

In the case of fatty acid ester hydrogenation a good selectivity, i.e. low linolenic acid content and a low content of fully saturated esters, could be achieved. This is especially important in the hydrogenation of triglycerides such as soybean oil and fish oil.

EXAMPLES I–III

Various amounts of gamma $A_2O_3$ having an inner surface area of 150 m²/g, a pore volume of 0.5 l/kg and consisting of spherical particles having a size of 60–70 micrometers were suspended, with vigorous stirring, in various 1000 ml amounts of an aqueous solution of a $Ni(NH_3)_6CO_3$ complex which contained 20 g nickel at a temperature of 50° C. The pH of the suspension was 10.2. The temperature was now increased within 30 minutes to about 90° C. with the aid of a heating coil. The precipitation was completed in 2 hours, the pH value then being 10.0, whereafter the catalyst suspension was filtered and the green cake was dried in an oven at a temperature of 120° C. for 16 hours. The green cake was subsequently calcined by increasing the temperature to 450° C. at a heating rate of 2 centrigrades per minute and maintaining it at 450° C. for half an hour, after which the catalyst was reduced and activated in a stream of hydrogen for 30 minutes at a gas-hour-space-velocity (GHSV) of 3000 hrs-1 and a temperature of 500° C. The properties are given below in Table 1.

TABLE 1

| Ex. | Nickel (wt. %) | Surface Ni (m²/g Ni) | DNi* (nm) | DR** (%) | m**** |
|---|---|---|---|---|---|
| I | 18 | 123 | 2.7 | 76 | 2.0 |
| II | 20 | 113 | 2.7 | 71 | 1.4 |
| III | 28 | 82*** | 4.1 | 78 | 1.8 |

\* = diameter Ni crystallites in nanometers
\*\* = degree of reduction under standard conditions (15 m³ $H_2$ (NTP) per kg Ni)
\*\*\* = calcined for 1 hr at 450° C. (no temperature programming)
\*\*\*\* = wear resistance As comparative example, Example 1 of U.S. Pat. No. 4,191,664 was repeated. In this case a wear resistance $m = 7.7$ was determined according to the method we used and a nickel surface area of 55 m²/g.

It will be appreciated that the higher the value of m, the more attrition takes place. Consequently low values of m are preferred. Table 1 shows that, according to the present invention, catalysts with an m value ranging between 1.4 and 2.0 were obtained, whereas a catalyst according to U.S. Pat. No. 4,191,664 showed an m value of 7.7. Consequently the catalysts according to the present invention represent an improvement over the art catalyst using the wear resistance test referred to earlier herein.

EXAMPLE IV

The dry green cake obtained as in Example II (dried at 120° C.) was impregnated with a saturated ammonium molybdate solution in water (containing 13.6% Mo), whereafter it was dried for 16 hours at 120° C. and calcined according to Example I. The catalyst was activated for 30 minutes at 500° C. The properties were as follows:

| Ni (%) | Mo (%) | SNi (m$^2$/g Ni) | DNi (nm) | DR (%) | m |
|---|---|---|---|---|---|
| 20 | 4 | 97 | 2.6 | 58 | 1.4 |

EXAMPLE V AND VI 102.6 kg gamma-aluminiumoxide as described in Example I was added in 25 minutes, under stirring, to 1572 kg of an aqueous solution of Ni(NH$_3$)$_6$CO$_3$ that contained 34.6 kg nickel. The temperature was now increased in 2 hours up 90° C. and thereafter heating was continued for 5 hours to a final temperature of 100° C. The pH dropped from 10.2 to 9.8. After filtration, the green cake was dried in a Heraeus drying oven for 16 hours at 120° C., ground in a mixer and subsequently calcined under nitrogen for 45 minutes at 400° C. The properties are given below:

| Ni (%) | SNi (m$^2$/g Ni) | DNi (nm) | DR (%) |
|---|---|---|---|
| 21 | 95 | 3.0 | 75 |

The calcined catalyst was impregnated with an aqueous solution of ammonium hepta-molybdate (containing 13.6% Mo), whereafter it was dried for 16 hours at 120° C. and calcined 1 hour at 450° C. After activation for 30 min. at 500° C., a catalyst was obtained having the following properties:

| Ni (%) | Mo (%) | SNi (m$^2$/g Ni) | DNi (nm) | DR (%) | m |
|---|---|---|---|---|---|
| 19.0 | 6.5 | 90 | 3.8 | 75 | 1.7 |

EXAMPLE VII

A methanation reaction was carried out as follows: A gas mixture consisting of H$_2$ and CO in relative amounts of 3.0:1 was passed for 18 days at a pressure of 3000 k Pa and a temperature of 480° C. over a catalyst prepared as in Example II, which subsequently had been impregnated with a solution of ammonium heptamolybdate containing 13.6% of Mo, which catalyst finally contained 21% of Ni and 13.6% of Mo. The volume of gas (1) per amount of catalyst (1) per hour was 2400. The conversion of the CO remained in this period above 99%, while the selectivity for the formation of methane very slowly dropped from 100% on the first day to 90% on the 15th day; at the same time the selectivity for the formation of CO$_2$ rose from 0 to 10% after 15 days.

EXAMPLE VIII a-f 50 g of a preshaped gamma-alumina (spheres, extrudates, quadrulopes; see specification in Table 2) were added to 100 ml Ni(NH$_3$)$_6$CO$_3$ solution containing 5 wt. % Ni. The temperature was increased to 60° C., causing a slow decomposition of the hexamine nickel(II) carbonate complex with simultaneous release of NH$_3$ and CO$_2$. Over a period of 10 to 20 h, Ni(OH)$_{2-2x}$(CO$_3$)$_x$ precipitates onto the internal and external surface areas of the support. The end point of the precipitation is clearly indicated by decoloration of the initially blue solution of the Ni-complex. The final pH was about 9.8, the initial pH about 11.2. It appeared that vigorous stirring of the solution is not beneficial as collisions between stirrer and alumina particles caused formation of fines by abrasion.

The catalyst particles were washed and dried in an oven at 120° C.

EXAMPLE IX

The same procedure was applied as in Example VIII(a), except that the temperature was 90° C. The precipitation took 1-4 h.

EXAMPLE X

The same procedure was applied as in Example VIII(a), except that Ni(NH$_3$)$_6$CO$_3$ solutions containing 2.2 wt. % Ni were used at a temperature of 80° C. The precipitation time was 24 h.

EXAMPLE XI

Concentrated solutions of Ni(NH$_3$)$_6$CO$_3$ complex, containing 10 wt. % of Ni, were used to impregnate the alumina support by the method of pore filling. The impregnated support was heated to 70° C. in an oven and Ni(OH)$_{2-2x}$(CO$_3$)$_x$ precipitated from the Ni-complex solution in the pores under simultaneous release of NH$_3$ and CO$_2$ Afterwards the catalyst was dried at 120° C.

TABLE 2

| Preshaped aluminas applied in Examples VIII to XI | | | |
|---|---|---|---|
| Surface area (m$^2$/g) | Pore volume (ml/g) | Shape | Size |
| A 320 | 0.45 | spheres | 2-4 mm |
| B 270 | 0.63 | spheres | 2-4 mm |
| C 100 | 0.51 | spheres | 2-4 mm |
| D 96 | 0.59 | extrudates | 5 × 1.5 mm |
| E 263 | 0.67 | extrudates | 5 × 1.7 mm |
| F 108 | 0.64 | quadrulopes | 10 × 4 mm |

TABLE 3

| Catalyst properties after precipitation onto preshaped gamma-alumina supports mentioned in Table 2 | | | | |
|---|---|---|---|---|
| Example | wt. % Ni | Active Surface Area (m$^2$/g Ni) | Average Ni crystallite size (nm) | Remarks |
| VIII | 8.1 | 152 | 2.5 | Support D |
| VIII | 6.8 | 203 | 1.9 | Support D |
| VIII | 7.4 | 205 | 2.0 | Support D, promoted with 1% Ba |
| VIII | 8.1 | 212 | 1.5 | Support F, promoted with 1% Ba |
| VIII | 17.9 | 234 | 1.5 | Support D |
| VIII | 17.3 | 223 | 1.5 | Support D |
| IX | 11.9 | 170 | 1.7 | Support D |
| X | 11.3 | 135 | 2.4 | Support D |

EXAMPLE XII

Fixed bed fatty acid hydrogenation

A fixed bed reactor, effective volume 0.2 l, made of stainless steel and suitable for a temperature up to 350°

C. and a pressure of 33,000 k Pa, was filled with 0.115 l of a catalyst prepared according to Example X. The catalyst consisted of 11.3 wt. % Ni-on-gamma-alumina extrudates and was reduced with hydrogen at 300° C. for 30 min. and then the temperature was increased at increments of 25° C. every 1/2 h up to 500° C. The active surface area of the reduced catalyst was 136 m²/g, based on Ni.

The catalyst was placed on 0.03 l of china rings and covered with 0.05 l of china rings, diameter 3 mm. Hydrogen was admitted up to a pressure of 3000 k Pa and the catalyst bed was heated to a temperature of 160° C. Then technical oleic acid, iodine value (IV) 95.5, Lovibond colour: 1 inch cell: Yellow 20.0, Red 2.2, was admitted to the top of the reactor at a rate of 0.115 l/h, corresponding to a liquid-hour-space-velocity (LHSV) of 1.0 and was continuously withdrawn from the bottom of the reactor. Hydrogen was supplied concurrently through the catalyst bed and continuously withdrawn at a rate of 30 l/h at atmospheric pressure and ambient temperature. The hydrogenated, snowy white fatty acids had IV=2 and contained only 3 mg Ni/kg of product. The experiment was continued for 80 hours; during this period the product-IV remained below 2 for a period of 50 hours and slowly increased to IV=20, showing a good active life of the catalyst.

EXAMPLE XIII

Fixed bed methanation activity

A tubular fixed bed reactor of 10 mm internal diameter was loaded with 5 g of catalyst prepared according to Example VIII. The catalyst consisted of gamma-alumina extrudates of 5 mm length and 1.5 mm diameter, containing 8 wt. % Ni. The catalyst was reduced according to the procedure given in Example XII, resulting in an active surface area of 152 m²/g, based on Ni. Prior to testing the catalyst particles were crushed to an average particle size of 1.5 mm.

Synthesis gas, containing 80% $H_2$ and 20% CO, was passed over the catalyst bed at a flow rate of 1040 ml/min, at a temperature of 500° C. and a pressure of 3000 k Pa. At regular intervals product gas samples were analyzed with GLC over a period of 14 days. During this period a 100% conversion was obtained and the only products observed were methane and water.

During the testing period the nickel surface area decreased to 94 m²/g and the average Ni crystallite size increased from 2.5 nm to 4.7 nm. The total surface area of the catalyst remained unchanged at 90 m²/g of catalyst.

EXAMPLE IV

Catalyst VIIIe, described in Table 2, was ground and sieved. A fraction of particle size below 30 micrometers was used for the hardening of fish oil. The catalyst was highly active and selective. In this test the following conditions were applied: Fish oil: initial iodine value 165; final iodine value 82; 250 g of fish oil; 0.1% nickel based on oil; 60 l $H_2$/h; pressure 100 k Pa; max. temperature 180° C.; stirrer speed 750 rpm. The hydrogenation time was 93 min., compared with 127 min. for a reference catalyst and the melting point of the hardened oil was 31° C., compared with 36° C. for the reference catalyst. This low melting point shows that the catalyst forms relatively low amounts of saturated triglycerides. A similar result was obtained when the catalyst was used in a fixed bed.

We claim:

1. A nickel upon transition alumina catalyst, containing 5 to 40 % (w/w) of nickel, characterized in that the catalyst has an active nickel surface area between 80 and 300 m²/g Ni and in which the nickel crystallites have an average diameter of 1 to 5 nanometers.

2. A nickel upon alumina catalyst according to claim 1, characterized in that the active nickel surface face area ranges between 100 and 250 m²/g Ni and an average nickel crystallite size of 1.5–3 nanometers.

3. A nickel upon alumina catalyst according to claim 1, characeized in that the transition alumina has a total surface area between 45 and 350 m²/g.

4. A process for the preparation of a nickel upon alumina catalyst according to claim 1, characterized in that a mixture of transition alumina in an aqueous solution of a nickel amine complex is heated to a temperature of 60°–100° C., as a result of which the precipitation of nickel hydroxide is caused, whereafter the catalyst suspension is separated, dried, calcined and, if need be, reduced.

5. A process according to claim 4, characterized in that the transition alumina ia gamma-alumina.

6. A process according to claim 4, charaterized in that the precipitation of the nickel hydroxide takes place in a pH range between 11.5 and 9.5.

7. A process according to claim 4, characterized in that the precipitation is carried out at a temperature between 75° and 95° C.

8. A process according to claim 4, characterized in that in the supported nickel catalyst also a metal compound is incorporated as promoter.

9. A process according to claim 8, characterized in that the metal compound is a molybdenum compound.

10. A process according to claim 8, characterized in that the desired amount of promoter in the catalyst is between 0.2 and 14% (w/w) in case of molybdenum.

11. A process according to claim 3 wherein the transition alumina has a total surface area between 75 and 250 m2/g.

12. A process according to claim 10 wherein the promoter in the catalyst is between 4 and 10% (w/w) in the case of molybdenum.

* * * * *